(12) United States Patent
Babenko et al.

(10) Patent No.: US 9,144,695 B2
(45) Date of Patent: Sep. 29, 2015

(54) ANTIPERSPIRANT COMPOSITIONS

(75) Inventors: Tamara Babenko, Bridgewater, NJ (US); Thomas Schamper, Cranbury, NJ (US); Salvatore J. Barone, Staten Island, NY (US); Juan Mateu, Oak Ridge, NJ (US); Irina Staina, Branchburg, NJ (US)

(73) Assignee: Coty Inc., New York, NY (US)

( * ) Notice: Subject to any disclaimer, the term of this patent is extended or adjusted under 35 U.S.C. 154(b) by 124 days.

(21) Appl. No.: 13/114,908

(22) Filed: May 24, 2011

(65) Prior Publication Data

US 2011/0293532 A1 Dec. 1, 2011

Related U.S. Application Data

(60) Provisional application No. 61/350,342, filed on Jun. 1, 2010.

(51) Int. Cl.
*A61K 9/12* (2006.01)
*A61K 8/28* (2006.01)
*A61Q 15/00* (2006.01)
*A61K 8/26* (2006.01)

(52) U.S. Cl.
CPC . *A61Q 15/00* (2013.01); *A61K 8/26* (2013.01); *A61K 8/28* (2013.01)

(58) Field of Classification Search
None
See application file for complete search history.

(56) References Cited

U.S. PATENT DOCUMENTS

| | | |
|---|---|---|
| 4,359,456 A | 11/1982 | Gosling et al. |
| 4,775,528 A | 10/1988 | Callaghan et al. |
| 5,330,751 A | 7/1994 | Curtin et al. |
| 5,939,055 A * | 8/1999 | Vu et al. .......... 424/65 |
| 6,074,632 A | 6/2000 | Shen |
| 6,136,302 A | 10/2000 | Juneja et al. |
| 6,274,127 B1 | 8/2001 | Schraer et al. |
| 6,436,381 B1 | 8/2002 | Carrillo et al. |
| 6,902,724 B1 | 6/2005 | Parekh et al. |
| 6,991,780 B2 | 1/2006 | Carrillo et al. |
| 7,087,220 B2 | 8/2006 | Li |
| 2006/0153788 A1 | 7/2006 | Swaile et al. |
| 2007/0110687 A1 | 5/2007 | Mattai et al. |
| 2007/0196302 A1 | 8/2007 | Pratt et al. |

FOREIGN PATENT DOCUMENTS

| | | |
|---|---|---|
| GB | 2048229 A | 12/1980 |
| WO | 0234223 A2 | 5/2002 |
| WO | 2006091417 A1 | 8/2006 |
| WO | 2009075678 A1 | 6/2009 |

OTHER PUBLICATIONS

"Antiperspirant Drug Products for Over-The-Counter Human Use; Final Monograph" U.S. Federal Register; Jun. 9, 2003, vol. 68; No. 110, pp. 34273-34293.
International Search Report and Written Opinion issued in corresponding International Application No. PCT/US2011/038557 dated Feb. 9, 2012 (10 pages).
2nd Office Action issued in corresponding Chinese Application No. 201180026928.1; Dated May 28, 2014 (11 pages).
Office Action issued in corresponding Chinese Application No. 201180026928.1; Dated Aug. 28, 2013 (14 pages).
Third Office Action (w/translation) issued in corresponding Chinese Application No. 201180026928.1; Dated Nov. 13, 2014 (9 pages).
Extended European Search Report issued Mar. 11, 2015 in corresponding European Application No. 11790281.7 (7 pages).

* cited by examiner

*Primary Examiner* — Mina Haghighatian
*Assistant Examiner* — Luke Karpinski
(74) *Attorney, Agent, or Firm* — Osha-Liang LLP

(57) ABSTRACT

An antiperspirant composition may include an aqueous carrier; and at least 4 to 7 weight percent of an aluminum and/or aluminum-zirconium antiperspirant active containing at least a Peak 4 specie. An antiperspirant composition may also include an aqueous carrier; and an aluminum and/or aluminum-zirconium antiperspirant active containing at least a Peak 4 specie, wherein the antiperspirant active contains less than 3 area percent Peak 1 and/or Peak 2 species from an HPLC chromatograph of the antiperspirant composition.

11 Claims, 2 Drawing Sheets

ANTIPERSPIRANT COMPOSITIONS

CROSS-REFERENCE TO RELATED APPLICATIONS

This application claims priority, under 35 U.S.C. §119, to U.S. patent application No. 61/350,342, filed on Jun. 1, 2010, which is herein incorporated by reference in its entirety.

BACKGROUND OF INVENTION

1. Field of the Invention

Embodiments disclosed herein relate generally to antiperspirant compositions. More particularly, embodiments disclosed herein relate to antiperspirant compositions having aluminum or aluminum-zirconium salts with high efficacy.

2. Background Art

Antiperspirant compositions are available in a variety of forms, such as aerosol suspensions; pump sprays; roll-on powders; emulsions or suspensions; and solid gels, waxes or suspensions.

Basic aluminum halides, particularly chlorides such as aluminum chlorohydrates, aluminum sesquichlorohydrate, aluminum dichlorohydrate, and the like, as well as aluminum nitrates, have been known and used for years as antiperspirant agents. In general, the aluminum compounds are complex structures comprised of mixtures of polymeric and monomeric compounds having various sizes and molecular structures, together with varying amounts of bound or coordinated water. The compounds can generally be represented by the simplified empirical formula, $Al_x(OH)_yY_{(3x-y)}$, where $0 < y \leq 3x$, $x \geq 1$, and Y is one or more of chloride, bromide, iodide, or nitrate ions. However, this empirical formula is simplified and is intended to include basic aluminum chlorides containing coordinated or bound molecules of water, as well as basic aluminum chloride polymers, complexes, and mixtures thereof. Aluminum chlorides where x is 2 and y is 1, i.e., $Al_2(OH)_5Cl$, is generally referred to as 5/6 basic aluminum chloride, and has been recognized as the standard active ingredient for antiperspirants for many years.

Aluminum chlorohydrates, as well as other aluminum salts, such as aluminum chlorohydrex (complexes of aluminum chlorohydrate with propylene glycol or polyethylene glycol) and aluminum zirconium glycine salts, are known to contain a variety of polymeric and oligomeric species with molecular weights ranging from 100 to 500,000.

The aluminum and/or zirconium salts are formed by partial neutralization of acidic aluminum ($Al^{3+}$) and/or zirconium ($Zr^{4+}$) metal ions. The partial neutralization of these ions results in the formation of aluminum and zirconium hydrolysis products of complex structure. The performance (i.e., efficacy) of aluminum and aluminum-zirconium salt compositions is dependent on the molecular distribution of these hydrolysis products. In general, low molecular weight hydrolysis products favor better performance by providing increased sweat inhibition, i.e., increased efficacy. Specifically, it has been clinically shown that the smaller the species, the higher the efficiency on sweat reduction.

Aluminum and aluminum-zirconium antiperspirant salts function by forming insoluble metal hydroxides in the ducts of sweat glands. This blockage prevents perspiration. Low molecular weight salts penetrate more deeply into these ducts than their high molecular weight counterparts. Thus, deeper penetration provides more effective blockage.

Accordingly, there exists a continuing need for developments in antiperspirant compositions having increased efficacy.

SUMMARY OF INVENTION

In one aspect, embodiments disclosed herein relate to an antiperspirant composition that includes an aqueous carrier; and at least 4 to 7 weight percent of an aluminum and/or aluminum-zirconium antiperspirant active containing at least a Peak 4 specie.

In another aspect, embodiments disclosed herein relate to an antiperspirant composition that includes an aqueous carrier; and an aluminum and/or aluminum-zirconium antiperspirant active containing at least a Peak 4 specie, wherein the antiperspirant active contains less than 3 area percent Peak 1 and/or Peak 2 species from an HPLC chromatograph of the antiperspirant composition.

Other aspects and advantages of the invention will be apparent from the following description and the appended claims.

DETAILED DESCRIPTION

In one aspect, embodiments disclosed herein relate to antiperspirant compositions having aluminum or aluminum-zirconium salts with high efficacy. In particular, embodiments disclosed herein relate to aqueous antiperspirant compositions that reduce, minimize, or prevent the conversion of a high efficacy specie that is generally considered to be unstable in aqueous systems to less desired low efficacy specie(s).

Figure 1:
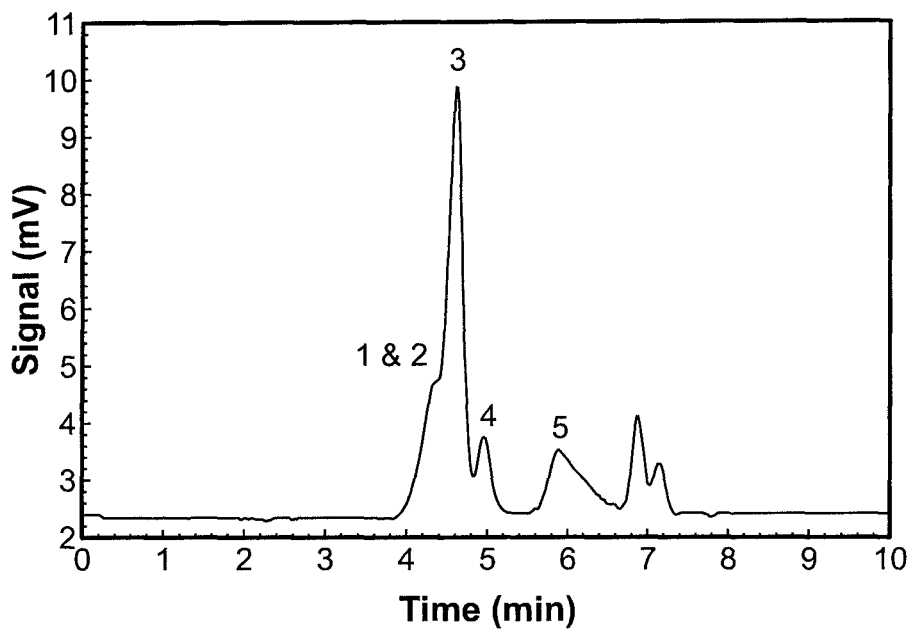
FIG. 1 shows an HPLC scan of a prior art antiperspirant salt.

High performance liquid chromatography (HPLC) employing size exclusion columns is commonly used to characterize the molecular weight distribution and efficacy of aluminum and aluminum-zirconium antiperspirant salts. Size exclusion chromatographic columns have a high affinity for low molecular weight materials and a low affinity for high molecular weight materials. This difference in affinity causes high molecular weight materials to be eluted more quickly than low molecular weight materials. Accordingly, this HPLC technique separates and identifies the components of aluminum and aluminum-zirconium antiperspirant salts with respect to molecular weight. Five distinct species have been identified by this technique. The highest molecular weight species is eluted first and referred to as Peak 1 material. The lowest molecular weight species is eluted last and referred to as Peak 5 material. FIG. 1 shows a HPLC diagram of a prior art aluminum antiperspirant salt. The relative area of each peak indicates the amount of the various components present. In this diagram Peaks 1 thru 3 have a greater relative area than Peaks 4 and 5, indicating that this sample is primarily composed of high molecular weight, low efficacy components. It is noted that some art refers to the term "band" instead of the term "peak" to describe the results of HPLC analysis. Under such terminology, Bands I, II, III and IV of one system generally correspond to Peaks 1+2 (together as Band I), 3, 4, and 5 of the other system, respectively.

As discussed above, lower molecular weight species, such as those eluted in Peaks 4 and 5, show greater efficacy at reducing sweat than higher molecular weight species, such as those eluted in the earlier peaks (Peaks 1, 2, and 3). Specifically, it has generally been considered that the low molecular weight species in Peak 4 and Peak 5 are responsible for increased sweat inhibition and enhanced efficacy that results when there is a preponderance of these peaks in the salt compositions. Species in Peak 3 will generally form a sizable portion of an antiperspirant composition, and provide significant antiperspirant effects; however, superior efficacy may generally obtained when the high molecular weight materials in Peaks 1 and 2 are minimized and low molecular weight materials in Peaks 4 and 5 are maximized.

However, many prior art references describe the instability of some of these high efficacy, low molecular weight species in water (particularly those species corresponding to Peak 4), resulting in the conversion of those high efficacy, low molecular weight species to the low efficacy, high molecular weight species (particularly those species corresponding to Peaks 1 and 2). Thus, salts having Peak 4 species have generally been avoided for use in aqueous antiperspirant systems due to this instability. However, the inventors of the present application have advantageously discovered that the concentration of the Peak 4 species may be maintained within an aqueous system by using a more dilute quantity of the aluminum or aluminum-zirconium salt. Specifically, by incorporating a lower aluminum or aluminum-zirconium salt concentration into an aqueous fluid, an equally efficacious product may unexpectedly result. Additionally, at such concentration levels, the equilibrium may also convert some quantity of any high molecular weight, low efficacy species present in the salt into low molecular weight, high efficacy species.

Whereas over-the-counter antiperspirant generally may have an active-ingredient concentration of anywhere from 10 to 25 weight percent calculated on an anhydrous basis in accordance with Title 21 of the U.S. Code of Federal Regulations, section 350.10 (the FDA requires that over-the-counter antiperspirants contain no more than 20 to 25 percent of the active ingredient, depending on the type of active), embodiments in accordance with the present application have a much lower concentration, yet may be just as effective as their higher concentration counterparts. In one embodiment, at least 4 to 7 weight percent on an anhydrous basis of an aluminum and/or aluminum-zirconium salt containing a quantity of Peak 4 species may be used in an aqueous antiperspirant composition, in accordance with the present disclosure. However, other embodiments may incorporate at least 4.5, 5.0, 5.2, 5.4, 5.6, 5.8, 6.0, 6.2, or 6.4 weight percent, and less than 6.8, 6.6, 6.4, 6.2, 6.0 weight percent, with suitable ranges including any of such lower limits and any of such upper limits. Further, one skilled in the art will appreciate, after reading the teachings contained in the present disclosure, that the preferred amount of salt may be higher than 7 weight percent or lower than that 4 weight percent, and the preferred concentrations may vary for different salts due to the difference in molecular composition (and relative amounts of different species) therebetween. Whereas the conventional approach to the formulation of antiperspirant compositions would dictate that a greater concentration of the active yields greater efficacy, the present inventors have surprisingly and unexpectedly discovered that for actives containing Peak 4 species within an aqueous carrier fluid, a lesser concentration yields equally good efficacy. For example, if the high efficacy species of a salt has a lesser relative amount of Peak 4 species, the optimal concentration (lowest concentration to produce substantially the same efficacy) range may be slightly higher than that mentioned above in order to result in a sufficient molar amount of Peak 4 species. Conversely, if the high efficacy species of a salt has a greater relative amount of Peak 4 species, then it might be suitable to use a slightly lower concentration of salt to achieve the same efficacy.

Alternatively, instead of referring to the total concentration of a salt, a salt may be incorporated into the aqueous carrier in an amount sufficiently low to minimize the formation of Peak 1 and 2 species, which may be detected on an HPLC chromatograph. For example, in accordance with embodiments of the present disclosure, an HPLC chromatograph of the antiperspirant composition may include less than 5 area percent of Peak 1 and/or Peak 2 species for the antiperspirant salt. Such values may be determined by performing an HPLC scan on a given antiperspirant composition and integrating the peaks corresponding to the antiperspirant salt species. In a particular embodiment, antiperspirant salt has less than 3 area percent of Peak 1 and/or 2 species on the HPLC chromatograph, and less than 2 area percent or less than 1 area percent in other embodiments. In yet another embodiment, the HPLC chromatograph of the antiperspirant composition may substantially free of Peak 1 and/or 2 species in the antiperspirant salt.

The types of aluminum and/or aluminum-zirconium salts that may be used in the present application include all those that are commonly considered antiperspirant active materials and covered by FDA Monograph as Category I antiperspirant actives and that contain aluminum or aluminum and zirconium. Antiperspirant actives are listed in the U.S. Federal Register issued Jun. 9, 2003, in Vol. 68, No. 110, pages 34273-34293, under the title "Antiperspirant Drug Products for Over-The-Counter Human Use; Final Monograph." Examples of suitable salts which can be used as starting materials include conventional aluminum and aluminum/zirconium salts, as well as aluminum/zirconium salts complexed with a neutral amino acid such as glycine, as known in the art. Suitable materials include (but are not limited to) aluminum chlorides (various types including, for example, anhydrous form, hydrated form, etc.), zirconyl hydroxychlorides, zirconyl oxychlorides, basic aluminum chlorides, basic aluminum chlorides combined with zirconyl oxychlorides and hydroxychlorides, and organic complexes of each of basic aluminum chlorides with or without zirconyl oxychlorides and hydroxychlorides and mixtures of any of the foregoing. These may include, but are not limited to, for example, aluminum chlorohydrate, aluminum chloride, aluminum chlorohydride, aluminum sesquichlorohydrate, aluminum chlorohydrol-propylene glycol complex, zirconyl hydroxychloride, aluminum zirconium trichlorohyrate, aluminum zirconium tetrachlorohyrate, aluminum zirconium pentachlorohyrate, aluminum zirconium octachlorohyrate, aluminum-zirconium glycine complexes (such as, for example, aluminum zirconium trichlorohydrex gly, aluminum zirconium tetrachlorohydrex gly, aluminum zirconium pentachlorohydrex gly, and aluminum zirconium octochlorohydrex gly), aluminum dichlorohydrate, aluminum chlorohydrex propylene glycol complex (PG), aluminum chlorohydrex polyethylene glycol complex (PEG), aluminum dichlorohydrex PG, aluminum dichlorohydrex PEG, aluminum sesquichlorohydrex PG, aluminum sesqichlorohydrex PEG, aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, nitrate derivatives thereof, bromide derivatives thereof, sulfate derivatives thereof, or mixtures thereof. These aluminum-containing materials may be commonly referred to as antiperspirant active aluminum salts, and an antiperspirant composition may include one or more of such salts. Such antiperspirant actives are commercially available from a number of manufacturers, including, for example, Summit Research Labs.

The antiperspirant compositions of the present disclosure may include an antiperspirant active at the levels described herein within an aqueous carrier. In various embodiments, the aqueous carrier may be present in the antiperspirant composition in an amount ranging from about 60 to 95 weight percent, from about 75 to 95 weight percent, or from about 85 to 95 weight percent. The aqueous antiperspirant compositions of the present disclosure may also include any additional skin active ingredients or material known or otherwise suitable for use in topical antiperspirant and deodorant compositions. Nonlimiting examples include solid or liquid carriers, surfactants or other wash-off aids, deodorant actives (e.g., antimicrobials, adsorbents, deodorant perfumes), fragrances, chelating agents, residue masking agents, other skin active agents, moisturizers or emollients, inert solids such as talc or solid polyethylene, thickeners, propellant, preservatives, processing aids, dyes or other colorants, or suspending agents.

The antiperspirant compositions of the present invention may be formulated into any solid, semi-solid or liquid product form suitable for topical application to the underarm or other area of the skin where application is desired. Nonlimiting examples of suitable product forms include gel or sticks; soft solids, lotions, or creams; roll-ons; and aerosol or pump sprays.

The antiperspirant compositions of the present application, all of which contain the foregoing active, may be applied topically to the underarm or other area of the skin in an amount effective to treat or reduce perspiration wetness and/or malodor. For example, the composition may be applied in an amount ranging at least from about 0.1 gram and no more than from about 20 grams, no more than from about 10 grams, or no more than from about 1 gram, to the underarm or other desired area of the skin. The compositions may applied to the underarm or other area of the skin, one or two times daily, or twice daily, to achieve effective antiperspirant and/or malodor control over an extended period.

The antiperspirant effect is achieved by the release of antiperspirant actives into the sweat. Aluminum-based salts may react with the electrolytes in the sweat to form a hydroxide complex (or plug) in the duct of the eccrine sweat gland at the opening of the epidermis, the top layer of the skin. The aluminum ions may also react with cell debris, as well as interact with the keratin fibrils in the sweat ducts to form a physical plug that prevents sweat from reaching the skin's surface. The plugs that have been formed prevent the gland from excreting liquid, but are removed over time by the natural sloughing of the skin. Aluminum salts may also have a slight astringent effect on the pores, causing them to contract and further prevent sweat from reaching the surface of the skin. The blockage of a large number of sweat glands may reduce the amount of sweat produced in the underarms, though this may vary from person to person.

EXAMPLE

Example 1

Different concentrations of an antiperspirant active (REACH AZO-956G, available from Summit Research Labs (Huguenot, N.Y.), which is a 36% w/w solution of aluminum-zirconium octachlorohydrex, were formulated into three antiperspirant compositions. The formulations of the three samples is shown in Table 1 below with the wet weight percent amounts being given. BRIJ® 72 is a polyoxyethylene (2) stearyl ether available from Croda Inc. (Edison, N.J.); INCROQUAT™ Behenyl TMS is a cationic emulsifier available from Croda Inc; DOW CORNING® 245 Fluid is a cyclosiloxane liquid from Dow Corning Corporation (Midland, Mich.), DOW CORNING® 200 Fluid 1000 CST is a silicone fluid available from Dow Corning Corporation; SF™ 1214 is a silicone fluid available from Momentive Performance Materials (Albany, N.Y.); and KF-8018 is aminopropyl dimethicone dispersed in cyclopentasiloxane, available from Shin-Etsu Chemical Co. (Tokyo, JP); and Reach AZO-956G is an aluminum octachlorohydrate gly solution available from Summit Research Labs (Huguenot, N.Y.). The moisture complex is described in U.S. patent Publication No. 2009/0087396, which is assigned to the present assignee and herein incorporated by reference in its entirety.

TABLE 1

| Components | Sample 1 (6% active) | Sample 2 (11.5% active) | Sample 3 (12.5% active) |
|---|---|---|---|
| Deionized Water | 77.63 | 61.21 | 58.23 |
| Brij 72 | 1.5 | 1.5 | 1.5 |
| Incroquat Behenyl TMS | 1.5 | 1.5 | 1.5 |
| DC 245 Fluid | 0.1 | 0.1 | 0.1 |
| DC 200 Fluid 1000 CST | 0.2 | 0.2 | 0.2 |
| SF 1214 | 0.1 | 0.1 | 0.1 |
| KF 8018 | 0.01 | 0.01 | 0.01 |
| REACH AZO-956G | 17.91 | 34.33 | 37.31 |
| moisture complex | 0.05 | 0.05 | 0.05 |
| rragrance | 1.0 | 1.0 | 1.0 |

Figure 2:
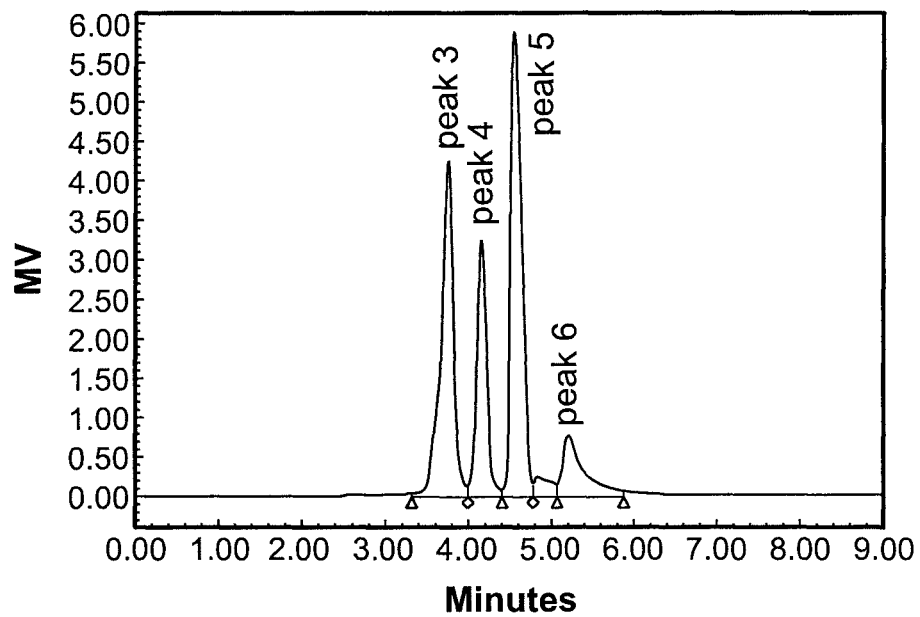
FIG. 2 shows an HPLC scan of an antiperspirant composition in accordance with one embodiment of the present disclosure.
Figure 3:
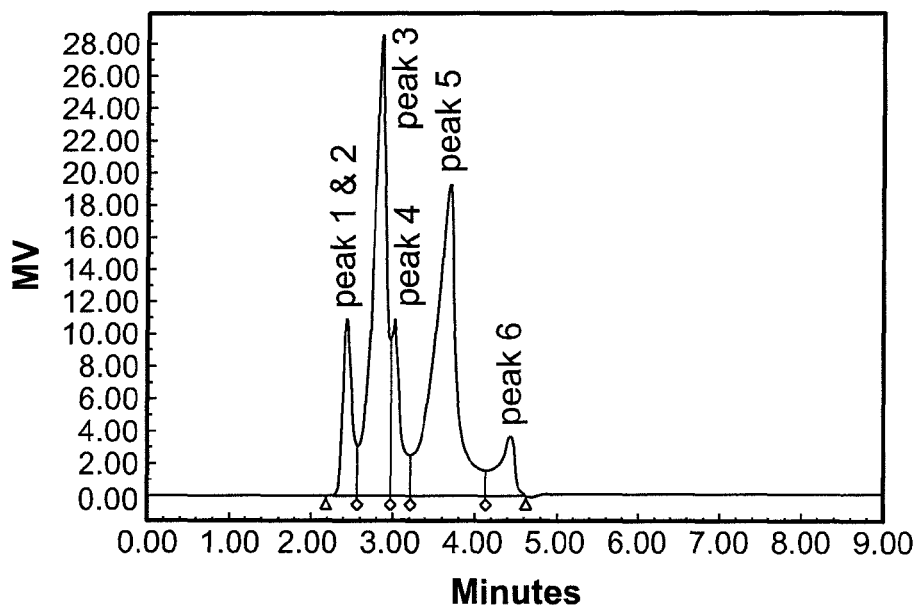
FIG. 3 shows an HPLC scan of a comparative antiperspirant composition.
Figure 4:
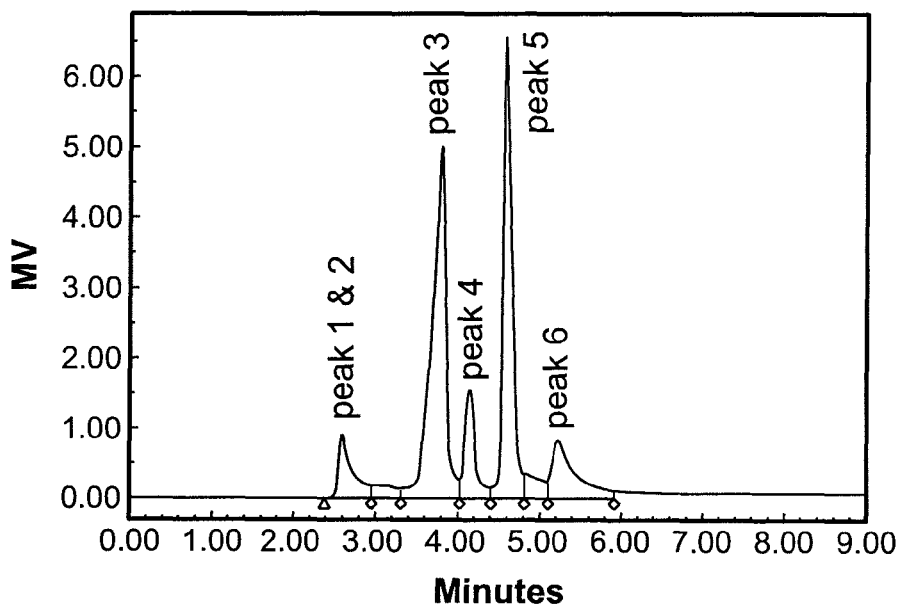
FIG. 4 shows an HPLC scan of a comparative antiperspirant composition.

Each of the samples were subjected to HPLC analysis, and HPLC scans of each of the samples are shown in FIGS. 1 to 3, respectively. Additionally, the integration results (% area) for each of the peaks within the HPLC scans are shown in Table 2 below.

TABLE 2

| HPLC Peaks | Sample 1 (6% active) | Sample 2 (11.5% active) | Sample 3 (12.5% active) |
|---|---|---|---|
| Peak 1 + 2 | — | 6.85 | 9.09 |
| Peak 3 | 33.61 | 37.42 | 35.45 |
| Peak 4 | 20.14 | 9.11 | 9.21 |
| Peak 5 | 35.17 | 36.55 | 40.07 |
| Peak 6 | 11.08 | 10.06 | 6.18 |

Samples 1 and 2 were subjected to a sauna study with human participants to test the sweat reduction of the samples. For two weeks prior to the start of the study, panelists used a deodorant that was provided to them (UA30-57-1 Women's Clear Stick Deo), and they were asked not to use any other products under the arm other than the one provided to them. Products were applied by dispensing 0.3 g of product via Eppendorf Repeating Pipet into the panelists' gloved fingers. The panelist then rubbed the product into the designated underarm area and kept their arms raised for 5 minutes to allow the product to dry.

For each panelist, bags containing one folded Webril Pad were assembled. The label on each bag designated the panelists name, LEFT/RIGHT designation, and timepoint. The labels were color coded according to the predetermined left/right randomization. Webril Pads being used for the axilla treated with the control product were dotted with a black sharpie to aid in determining which pad would be placed in which bag on exiting the sauna. Each pre-labeled bag (containing the pad) was weighed 3× to the 3rd decimal place.

On Day 1, panelists reported directly to the spa. The panelists applied the products to their axilla according to the predetermined randomization (Application #1). The panelists kept their arms raised for 5 minutes while the product was allowed to dry.

On Day 2, panelists reported directly to the spa. The panelists applied the products to their axilla according to the predetermined randomization (Application #2). The panelists kept their arms raised for 5 minutes while the product was allowed to dry. Panelists were then instructed not to shower, shave, or apply any other product to the underarm area, and to return to the sauna the next morning On Day 3, panelists went directly to the sauna where pads were placed under the panelists' arms by a technician, and they were allowed to enter the sauna in a predetermined order. Panelists were instructed to bring their arms close to their body to hold the pads in place. Panelists remained seated in the sauna for 15 minutes. After the 15 minutes had elapsed, panelists exited the sauna in the order by which they entered. The pads were removed by the technician and placed in their respective bags. The technician examined the underarms of each panelist and made note of any redness or discomfort. Each pre-labeled bag (containing the pad) was weighed 3× to the 3rd decimal place. The approximate time elapsed from collection to weighing (should occur within 3 hours of collection) the pads is noted.

The average ratio for the twenty participants (g of sweat on pad/g product applied (0.3 grams in each case) for the 1 hour collection of Sample 1 was 0.578, whereas it was 0.670 grams for Sample 2, i.e., Sample 1 resulted in 14% less sweat collection than Sample 2. After 24 hours, the average ratio was 0.678 for Sample 1 and 0.768 for Sample 2, i.e., Sample 1 resulted in 12% less sweat collection than Sample 2. The collected data from the twenty participants is shown in Table 3A-3B.

TABLE 3A

Sample 1

| | 1 hr collection | | 24 hr collection | |
| --- | --- | --- | --- | --- |
| | Sweat on pad (g) | Ratio (sweat on pad/product applied) | Sweat on pad (g)/product applied (g) | Ratio |
| 1 | 0.195 | 0.650 | 0.212 | 0.707 |
| 2 | 0.089 | 0.297 | 0.028 | 0.092 |
| 3 | 0.031 | 0.103 | 0.681 | 2.270 |
| 4 | 0.222 | 0.740 | 0.213 | 0.711 |
| 5 | 0.214 | 0.713 | 0.158 | .0526 |
| 6 | 0.072 | 0.241 | 0.122 | 0.408 |
| 7 | 0.15 | 0.499 | 0.24 | 0.800 |
| 8 | 0.17 | 0.566 | 0.506 | 1.688 |
| 9 | 0.336 | 1.119 | 0.035 | 0.118 |
| 10 | 0.729 | 2.430 | 0.282 | 0.940 |
| 11 | 0.094 | 0.314 | 0.299 | 0.998 |
| 12 | 0.135 | .450 | 0.534 | 1.779 |
| 13 | 0.178 | 0.593 | 0.056 | 0.188 |
| 14 | 0.076 | 0.254 | 0.030 | 0.129 |
| 15 | 0.05 | 0.166 | 0.056 | 0.186 |
| 16 | 0.149 | 0.498 | 0.035 | 0.118 |
| 17 | 0.113 | 0.377 | 0.117 | 0.390 |
| 18 | 0.29 | 0.966 | 0.066 | 0.221 |
| 19 | 0.079 | 0.263 | 0.167 | 0.557 |
| 20 | 0.097 | 0.323 | 0.224 | 0.746 |

TABLE 3B

Sample 2

| | 1 hr collection | | 24 hr collection | |
| --- | --- | --- | --- | --- |
| | Sweat on pad (g)/product applied (g) | Ratio | Sweat on pad (g)/product applied (g) | Ratio |
| 1 | 0.163 | 0.543 | 0.156 | 0.520 |
| 2 | 0.128 | 0.427 | 0.037 | 0.124 |
| 3 | 0.045 | 0.150 | 0.99 | 3.299 |
| 4 | 0.153 | 0.510 | 0.288 | 0.961 |
| 5 | 0.204 | 0.680 | 0.109 | 0.364 |
| 6 | 0.075 | 0.250 | 0.179 | 0.596 |
| 7 | 0.159 | 0.530 | 0.31 | 1.033 |
| 8 | 0.309 | 1.030 | 0.454 | 1.514 |
| 9 | 0.324 | 1.061 | 0.117 | 0.389 |
| 10 | 0.815 | 2.717 | 0.183 | 0.610 |
| 11 | 0.102 | 0.340 | 0.349 | 1.163 |
| 12 | 0.146 | 0.486 | 0.604 | 2.014 |
| 13 | 0.178 | 0.588 | 0.092 | 0.307 |
| 14 | 0.076 | 0.254 | 0.04 | 0.134 |
| 15 | 0.056 | 0.187 | 0.049 | 0.163 |
| 16 | 0.145 | 0.482 | 0.033 | 0.109 |
| 17 | 0.165 | 0.549 | 0.148 | 0.492 |
| 18 | 0.605 | 2.016 | 0.082 | 0.274 |
| 19 | 0.08 | 0.268 | 0.21 | 0.700 |
| 20 | 0.096 | 0.320 | 0.178 | 0.594 |

Embodiments of the present disclosure may provide at least one of the following advantages. Embodiments in accordance with the present application may have a lower concentration of antiperspirant actives than those typically used in the art, yet such embodiments may be just as effective as their higher concentration counterparts. Specifically, whereas the conventional approach to the formulation of antiperspirant compositions would dictate that a greater concentration of the active yields greater efficacy, the present inventors have surprisingly and unexpectedly discovered that for actives containing Peak 4 species within an aqueous carrier fluid, a lesser concentration yields equal efficacy based on the equilibrium between the Peak 4 species and less effective Peak 1 and/or 2 higher molecular weight species in an aqueous fluid.

Many prior art references describe the instability of Peak 4 species in water (resulting in the conversion of those high efficacy, low molecular weight species to the low efficacy, high molecular weight species corresponding to Peaks 1 and 2), thus encouraging use of actives containing Peak 4 species within non-aqueous carriers. However, the inventors of the present application have advantageously discovered that the concentration of the Peak 4 species may be maintained within an aqueous system by using a more dilute quantity of the aluminum or aluminum-zirconium salt. Specifically, by incorporating a lower aluminum or aluminum-zirconium salt concentration into an aqueous fluid, a more efficacious product may unexpectedly result. Additionally, at such concentration levels, the equilibrium may also convert some quantity of any high molecular weight, low efficacy species present in the salt into low molecular weight, high efficacy species.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed:

1. An antiperspirant composition, comprising:
an aqueous carrier comprising water; and
a solution of antiperspirant active that provides an aluminum and/or aluminum-zirconium antiperspirant active;

wherein the antiperspirant composition includes about 60 to 95 percent aqueous carrier including about 58 to 78 percent water, 5 to 7 weight percent antiperspirant active and at least a Peak 4 specie, wherein from an HPLC chromatograph of the antiperspirant composition, the antiperspirant active contains an area for the Peak 4 species that is at least twice an area for Peak 1 and 2 species.

2. The antiperspirant composition of claim 1, wherein the aluminum and/or aluminum-zirconium antiperspirant active is present in an amount ranging from at least 5.7 to 6.3 weight percent of the antiperspirant composition.

3. The antiperspirant composition of claim 1, wherein the antiperspirant active comprises less than 5 area percent Peak 1 and/or Peak 2 species from an HPLC chromatograph of the antiperspirant composition.

4. The antiperspirant composition of claim 3, wherein the antiperspirant active contains less than 2 area percent Peak 1 and/or Peak 2 species from an HPLC chromatograph of the antiperspirant composition.

5. The antiperspirant composition of claim 4, wherein the antiperspirant active contains substantially no Peak 1 and/or Peak 2 species from an HPLC chromatograph of the antiperspirant composition.

6. The antiperspirant composition of claim 1, further comprising at least one of nonionic, cationic, or anionic surfactants, wash-off aids, deodorant actives, fragrances, chelating agents, residue masking agents, skin active agents, moisturizers, emollients, inert solids, thickeners, propellant, preservatives, processing aids, dyes, suspending agents, conditioning agents.

7. The antiperspirant composition of claim 1, wherein the aqueous carrier is present in an amount ranging from about 75 to 95 weight percent of the composition.

8. The antiperspirant composition of claim 7, wherein the aqueous carrier is present in an amount ranging from about 85 to 95 weight percent of the composition.

9. The antiperspirant composition of claim 1, wherein the antiperspirant active is selected from aluminum-zirconium octachlorohydrex, aluminum chlorohydrate, and combinations thereof.

10. The antiperspirant composition of claim 1, wherein the aluminum and/or aluminum-zirconium antiperspirant active is an aluminum and/or aluminum-zirconium halide, hydroxyhalide, and/or oxyhalide antiperspirant active.

11. The antiperspirant composition of claim 1, wherein the aluminum and/or aluminum-zirconium antiperspirant active is an aluminum and/or aluminum-zirconium chloride, hydroxychloride, and/or oxychloride antiperspirant active.

\* \* \* \* \*